(12) United States Patent
Odom

(10) Patent No.: US 7,209,791 B2
(45) Date of Patent: Apr. 24, 2007

(54) ELECTROMAGNETIC DELIVERY SYSTEM TO INFLUENCE A BIOLOGICAL SYSTEM

(76) Inventor: Joseph Odom, 23 Bell Ave. #8, San Anselmo, CA (US) 94960

( * ) Notice: Subject to any disclaimer, the term of this patent is extended or adjusted under 35 U.S.C. 154(b) by 119 days.

(21) Appl. No.: 10/899,562

(22) Filed: Jul. 27, 2004

(65) Prior Publication Data

US 2006/0293726 A1   Dec. 28, 2006

Related U.S. Application Data

(60) Provisional application No. 60/495,266, filed on Aug. 16, 2003.

(51) Int. Cl.
  *A61N 1/18* (2006.01)
  *A61N 1/00* (2006.01)

(52) U.S. Cl. ................. 607/75; 607/2; 607/35

(58) Field of Classification Search ............. 607/75, 607/139, 144, 152, 149, 2
See application file for complete search history.

(56) References Cited

U.S. PATENT DOCUMENTS 6,149,672 A    11/2000  Ruschke
6,272,383 B1 *  8/2001  Grey et al. ............... 607/72

OTHER PUBLICATIONS

Article from Seventh Symposium of the Society for Acupuncture Rsearch Oct. 2000 "Preliminary Reults of Research in the Use of Bio-transducers in Acupuncture", p. 42.
Print of website page, Ito Co. Ltd. (www.itolator.co.jp), referring to Dr. Manaka's ion pumping cords, referenced in the specification.

* cited by examiner

*Primary Examiner*—Robert E. Pezzuto
*Assistant Examiner*—Tammie K. Heller
(74) *Attorney, Agent, or Firm*—Thomas M. Freiburger

(57) ABSTRACT

A wearable device for transmitting the resonant frequency of a solution to a biological system with the purpose of having a positive health influence on the biological system. Electrodes capable of conducting a small electrical current are placed in contact with the skin of an animal or human. These electrodes are connected to wires with an inline diode. A current results from the difference in electric potential of the two distal points on the skin, rectified into DC by the diode. Each wire is connected to one of two conducting leads. The leads are separated and submerged in a solution which has conducting properties. The current is modulated by the substance in solution and transmits this modulated current to the electrodes where the electromagnetic signature is transferred to the body. Thus by changing the substance in the solution the energy sensed by the body will differ. Careful and correct choice of the substance in solution will have positive influence on the health of the biological system. The preferred embodiment for the device is a necklace, bracelet, anklet or dermal patch.

15 Claims, 2 Drawing Sheets

# ELECTROMAGNETIC DELIVERY SYSTEM TO INFLUENCE A BIOLOGICAL SYSTEM

This application claims benefit of provisional application No. 60/495,266, filed Aug. 16, 2003.

BACKGROUND OF THE INVENTION

This invention concerns transmission of resonant electromagnetic frequency of substances in solution to a biological system, such as the human body, by way of a wearable appliance such as a necklace.

The cells of a biological system have electrical charges. These can be measured and are not in constant state. That is to say voltage, waveform and electrical potential will vary over time. Therefore when connected by a conducting medium an incoherent flow results.

Yoshio Manaka overcame this problem by inserting a low resistance diode inline with a low resistance wire to rectify the incoherent current into direct current. This device has been in commerce for years, using a conducting wire with an inline diode to transmit ionic energy from one area of a biological system to another, sold in the U.S. as "Manaka Ion Pumping Cords". Such cords have been used successfully for many years in acupuncture; areas of excess positive ions are thereby shunted to areas of negative ionic charge with the purpose of reducing pain and inflammation.

A number of devices exist which influence biological systems, human or animal, by use of electromagnetic or magnetic energy. These devices use specific electromagnetic frequencies and/or waveforms produced by an outside source of electricity or outside magnetic sources. The cells of a mammalian biological system operate on micro voltages. These devices use voltages many times higher. It has been stated by Robert o. Beker, M.D. and others that higher voltages overwhelm the cells of a biological system and that subtle health effects are lost.

Any substance has a specific resonant frequency or electromagnetic signature. This can be measured by a number of devices, including resonance ionization spectroscopy, atomic absorption, and fluorescence spectroscopy. An attempt to impart the electromagnetic resonance frequency of substances in solution to a biological system was made in U.S. Pat. No. 6,149,672 to Ruschke using a laser device.

Another device with a similar objective was described in the Seventh Symposium of the Society for Acupuncture Research, October 2002, page 42.

The prior art did not contemplate electrodes paced on the body. It used needles inserted into the body. It required licensed health care professionals to operate, could not be used for extended periods of time and was not portable. It was not obvious that the device would work by placing electrodes on the skin surface because different electrical capacitance properties exist on cell walls of dermal tissue as compared to deeper tissue.

Recently an AIDS patient suffering with peripheral neuropathy would experience pain relief with correctly placed acupuncture needles connected to the device described in the Seventh Symposium of the Society for Acupuncture Research, cited above, when a solution of ascorbic acid at pH 4.2 was used. This pain relief would last about 24 hours. Returning daily to the clinic for this treatment was not practical for this person. Pursuant to the current invention a device was constructed using gold-plated electrodes to be placed directly on the skin in place of the inserted acupuncture needles. The patient could thus be treated at home and could self regulate how often to be treated. This individual reported a similar positive effect of pain relief with the invention. Similar portable devices can be used with individuals with arthritis and back pain and prove effective.

SUMMARY OF THE INVENTION

Accordingly, a first objective of the invention is to influence a biological system with the resonant electromagnetic frequency of substances in solution to promote health.

It is a second objective to influence a biological system by use of the electrical potential of the cells of the system itself.

Accordingly, as regards the first object, the invention provides an apparatus by which a DC current is passed through a substance that has the ability to conduct electric current. This is accomplished by passing the current between two leads which are able to conduct the current. The substance in the solution is chosen to have a positive influence on health; this substance may be a vitamin, herb, mineral, homeopathic, medicine, essential oil or other useful substance. The solution may be aqueous, lipid or alcohol.

As regards the second objective, any two places on the surface of a human or animal have different electrical potential. Connecting the places with a conducting material will not produce a useful current; the addition of a diode inline is necessary to rectify this incoherent current to useful direct current.

The device uses a necklace as the preferred embodiment, a wearable pendant with an artful design.

Further objects and advantages of the invention will become apparent from a consideration of the drawings and descriptions.

DESCRIPTION OF THE PREFERRED EMBODIMENTS

Figure 1:
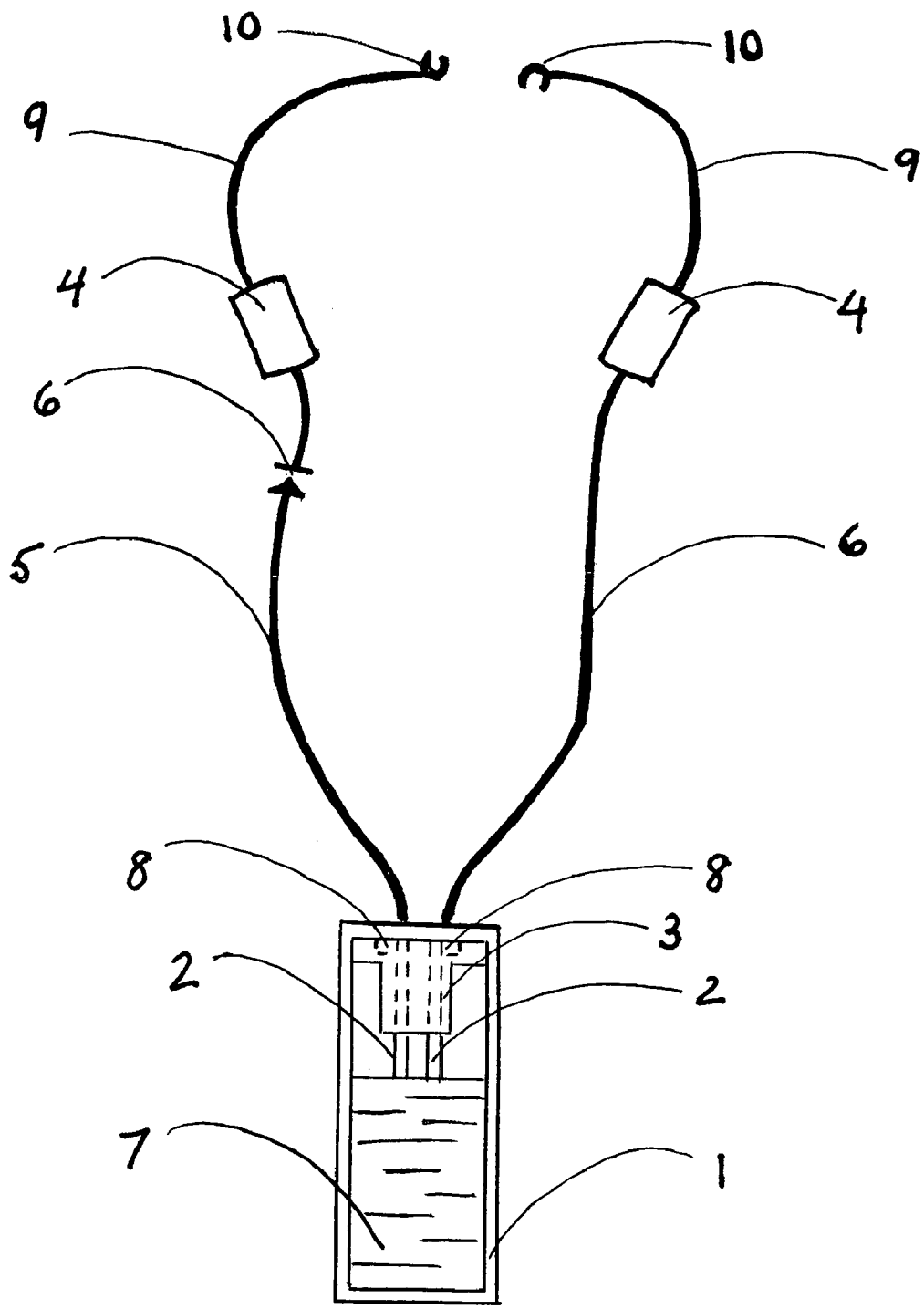
FIG. 1 is a front elevation view of a necklace according to the invention including a container with a solution shown.
Figure 2:
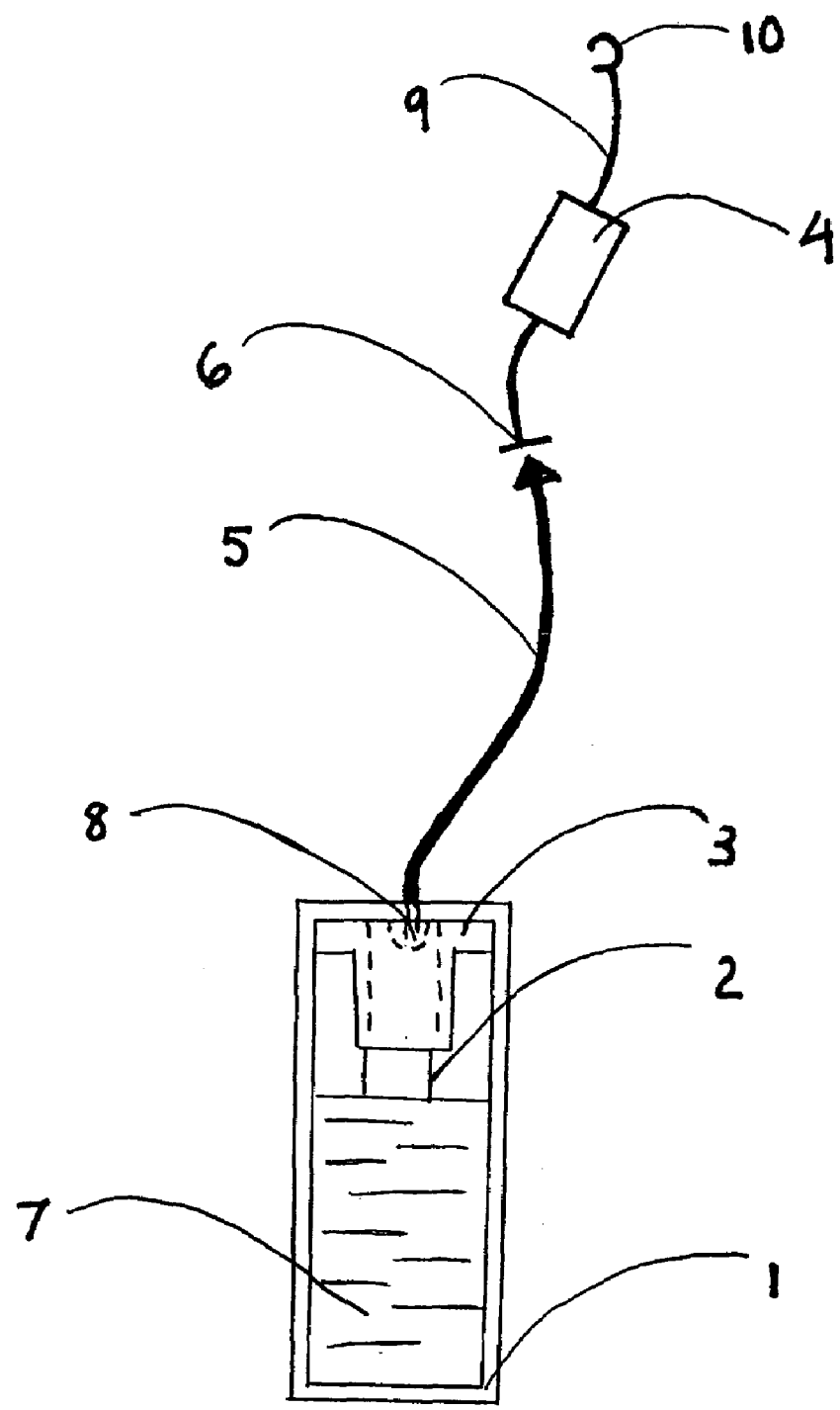
FIG. 2 is a side elevation view partially in section showing the invention.

A preferred embodiment of the device is a wearable necklace as illustrated in FIGS. 1 (front elevation) and 2 (side elevation).

The necklace has a cell 1 (i.e. a container or vial) made of glass, plastic or other material capable of holding liquid. The container is closed at both ends and is watertight. This container has within it twin parallel leads 2. These leads are made of a material that can conduct an electrical charge and may be plates that are in parallel plane to each other. An insulating material 3 separates the conducting plates, holding them in position. Connected at 8 to the conducting plates 2 are low resistance wires 5. In line with one wire 5 is a low forward current diode 6. The wire 5 has attached to it beads or plates 4 made of a conductive material. The beads or plates 4 act as electrodes and touch the skin of the human or animal. The necklace is fastened by non-conductive string 9 above the plates 4, attached to a standard jewelry clasp 10.

Any two points on the skin of a biological system, such as a human body, have a different electrical potential. This charge, however, is not in a constant state. Using a low forward current diode 6 in line rectifies this into direct current. This DC current flows through a low resistance wire 5 to the conducting plates 2. The leads or plates preferably are placed parallel and separated by a nonconductive material, i.e. the insulator 3. The leads are submerged in the container 1, in a solution 7. The solution is capable of conducting an electrical current. Two electrodes 4 of the necklace touch the epidermis. The resultant DC current flows to the conducting plates or leads and through the solution, picking up the electromagnetic resonance frequency or "signature" of the substance 7 in solution producing a kind of resonant frequency circuit. This resonant frequency is transmitted to the biological system by way of the electrodes 4.

The electromagnetic signature of a substance such as vitamin C has a positive influence on health when induced into a biological system in this manner.

This device is also constructed so as to be used with any two points of a body that may be connected with wires. This may include but is not limited to rings; the ring is constructed of a non-conductive material and has embedded in its inner side conductive plates connected to the device. Solutions are used to ease the pain of arthritis and/or promote local healing of the finger. A similar ring is used with a vasodilator on the penis to correct erectile dysfunction. Arm bands and bracelets are constructed of non-conductive elastic material and have embedded in the side contiguous to the skin conductive electrodes that are connected to the device. Solutions are used which ease pain and promote healing. Elbow bands, knee bands, ankle bands and headbands are similarly constructed. The earpieces of eyeglasses are made of conductive material and the device is embedded in the frame of the glasses. Electrically conductive dermal patches can carry or be connected to the device and used where local healing is needed in the body. The device may have in line a switching mechanism to turn the current on and off as well as a variable voltage device to regulate the current. This device may include a second diode on the second wire. The electrodes may be connected directly to the leads, usually but not necessarily on a smaller device such as a ring or patch. Necklaces or other appliances can also be made this way.

The above described preferred embodiments are intended to illustrate the principles of the invention, but not to limit its scope. Other embodiments and variations to this preferred embodiment will be apparent to those skilled in the art and may be made without departing from the spirit and scope of the invention as defined in the following claims.

I claim:

1. A method for transmitting a resonant frequency of a substance to a biological system using the energy of the biological system, comprising:
   selecting a substance to produce a desired therapeutic effect, and placing the substance in solution,
   providing a liquid-tight vial containing the selected substance in a conductive solution and having two spaced apart, conductive metal leads in the solution, with two conductive wires extending from the vial, each being connected to one of the conductive leads, and with a conductive, non-penetrating skin contact electrode connected to each of the wires, each electrode being capable of making electrical contact with the skin or other living cells at the surface of the biological system,
   providing a diode in line with one of the wires, to rectify incoherent current flowing in the wires into direct current, and
   attaching the electrodes to a biological system such that the electrodes make electrical contact with the skin or other living cells at the surface of the biological system, to thereby establish a direct current flowing through the wires, the leads and the solution due to differing electrical potential at different points on the biological system, and thereby modulating the electrical current in accordance with the resonant frequency of the conductive solution in the vial and thus having an effect on the biological system.

2. The method of claim 1, wherein the step of attaching the electrodes to a biological system comprises hanging the electrodes with the two wires and the vial, and with a connecting flexible line, over the neck of a human such that the electrodes make contact with the skin.

3. The method of claim 2, wherein the flexible line is connected to the two electrodes and extends around the neck.

4. The method of claim 1, wherein the substance in solution comprises ascorbic acid at 4.2 pH in distilled water, in treatment of a human for a condition such as pain caused by peripheral neuropathy.

5. The method of claim 4, wherein the device is worn four times a day for a one hour period each time.

6. The method of claim 1, wherein the substance in solution comprises the essential oil of lavender in vegetable glycerine, in treatment of a human for a condition such as pain and stiffness related to arthritis.

7. The method of claim 6, wherein such a device is worn three consecutive hours a day.

8. The method of claim 1, wherein the substance in solution comprises calcium citrate in distilled water, in treatment of a human for a condition such as anxiety, where worn for twenty minutes every two hours.

9. A wearable device for transmitting a resonant frequency of a substance to a human being using the energy of the human being to power the device, comprising:
   a substance in solution, a substance being selected to produce a desired therapeutic effect on the human being,
   a substantially liquid-tight vial containing the substance in solution and having two spaced apart, conductive metal leads in the solution, with two conductors extending from the vial, each being connected to one of the conductive leads, and with a conductive, non-penetrating skin contact electrode connected to each of the conductors, each electrode being capable of making electrical contact with the skin of the human being, and
   a diode in line with one of the conductors, to rectify incoherent current flowing in the conductors into direct current,
   whereby the wearable device can be worn on the human being such that the electrodes make electrical contact with the skin in a non-penetrating manner, to thereby establish a direct current flowing through the conductors, the leads and the solution due to differing electrical potential at different points on the biological system, and thereby modulating the electrical current in accordance with the resonant frequency of the conductive solution in the vial and thus having an effect on the biological system.

10. The device of claim 9, wherein the device is in the form of a necklace with the electrodes positioned to make contact with the skin on the back of the neck, near the shoulders of a human being.

11. The device of claim 9, wherein the device is in the form of a bracelet with the electrodes positioned to make contact with the skin of a human being.

12. The device of claim 9, wherein the device is in the form of an anklet with the electrodes positioned to make contact with the skin of a human being.

13. The device of claim 9, wherein the device is in the form of a belt with the electrodes positioned to make contact with the skin of a human being.

14. The device of claim 9, wherein the device is in the form of a ring with the electrodes positioned to make contact with the skin of a human being.

15. The device of claim 9, wherein the device is in the form of a dermal patch with adhesive for securing to the skin.

* * * * *